United States Patent
Woods et al.

[11] 4,031,075
[45] June 21, 1977

[54] ALKYLATED PREGNANES AND PROCESS FOR OBTAINING SAME

[75] Inventors: Gilbert Frederick Woods, Glasgow; Robert Thomas Logan, Lanark; George McGarry, Airdrie; Robert Gibson Roy, Larkhall, all of Scotland

[73] Assignee: Akzona Incorporated, Asheville, N.C.

[22] Filed: Mar. 4, 1976

[21] Appl. No.: 663,893

Related U.S. Application Data
[63] Continuation of Ser. No. 487,336, July 10, 1974, abandoned.

[30] Foreign Application Priority Data
July 11, 1973 United Kingdom ............ 33149/73

[52] U.S. Cl. ............ 260/239.55 D; 260/239.55 R; 260/397.4; 260/397.45
[51] Int. Cl.² .............................. C07J 71/00
[58] Field of Search ........................ 260/397.45

[56] References Cited
UNITED STATES PATENTS
| | | |
|---|---|---|
| 3,718,542 | 2/1973 | Irmscher et al. ............ 260/397.45 |
| 3,755,303 | 8/1973 | Nathansohn .................. 260/397.45 |
| 3,862,194 | 5/1975 | Woods et al. ................ 260/397.45 |

*Primary Examiner*—Elbert L. Roberts
*Attorney, Agent, or Firm*—Francis W. Young; Hugo E. Weisberger

[57] ABSTRACT

The invention relates to novel 21-alkylated steroids of the pregnane series having the formula:

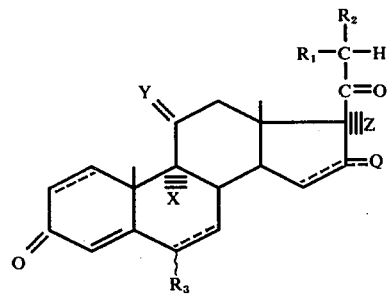

wherein
 $X = H$ or halogen;
 $Y = H_2$, H(OH), H(Oacyl), O or H(halogen);
 $R_1 =$ an alkyl group having 1-4 C-atoms;
 $R_2 = R_1$ or H;
 $R_3 = H$, $CH_3$ or halogen;
 $Z = $ OH, Oalkyl or Oacyl or form together with $R_4$ a group as indicated below;
 $Q = $ (when $C_{15}$-$C_{16}$ is saturated) alkylidene having 1-4 C-atoms or ($\beta$H) ($\alpha R_4$), in which $R_4$ together with Z is alkylidenedioxy having 3-5 C-atoms, alkylidene having 1-4 C-atoms, aralkylidene having 7-8 C-atoms, alkylene of the formula

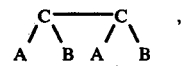

wherein $A = H$ or halogen and $B = H$, halogen, alkyl (1–4 C), haloalkyl, alkoxy or phenyl, or a [17α,16α-d]- or [16α,17α-d]-oxazolino-group, wherein the C-atom in 2'-position may be substituted by alkyl (1–4 C) or phenyl; or Q = (when $C_{15}$-$C_{16}$ is unsaturated) methyl or halomethyl, and a process for obtaining same.

The novel compounds possess strong anti-inflammatory properties and are useful in the treatment of inflammatory conditions especially those associated with the skin and allergic reactions.

6 Claims, No Drawings

ALKYLATED PREGNANES AND PROCESS FOR OBTAINING SAME

This application is a continuation of application Ser. No. 487,336, filed July 10, 1974, and now abandoned.

The present invention relates to novel 21-alkylated steroids of the pregnane series and to processes for their preparation.

More particularly, the invention relates to novel 21-alkylated steroids of the formula:

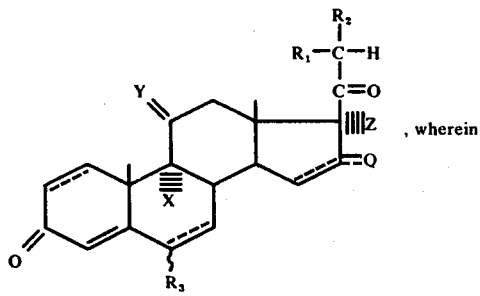

X = H or halogen;
Y = $H_2$, H(OH), H(Oacyl), O or H(halogen);
$R_1$ = an alkyl group having 1–4 C-atoms;
$R_2$ = $R_1$ or H;
$R_3$ = H, $CH_3$ or halogen;
Z = OH, Oalkyl or Oacyl or forms together with $R_4$ a group as indicated below;
Q = (when $C_{15}$-$C_{16}$ is saturated) alkylidene having 1–4 C-atoms or ($\beta$H) ($\alpha R_4$), in which $R_4$ together with Z is alkylidenedioxy having 3–5 C-atoms, alkylidene having 1–4 C-atoms, aralkylidene having 7–8 C-atoms, alkylene of the formula

wherein A = H or halogen and B = H, halogen, alkyl (1–4 C), haloalkyl, alkoxy or phenyl, or a [17$\alpha$, 16$\alpha$-d]- or [16$\alpha$, 17$\alpha$-d]-oxazolino-group, wherein the C-atom in 2'-position may be substituted by alkyl (1–4 C) or phenyl; or Q = (when $C_{15}$-$C_{16}$ is unsaturated) methyl or halomethyl: $C_1$-$C_2$ and $C_6$-$C_7$ may be saturated or unsaturated; and halogen being preferably F or Cl.

Of particular importance are the 21-alkylated pregnane compounds according to the invention having the partial formula

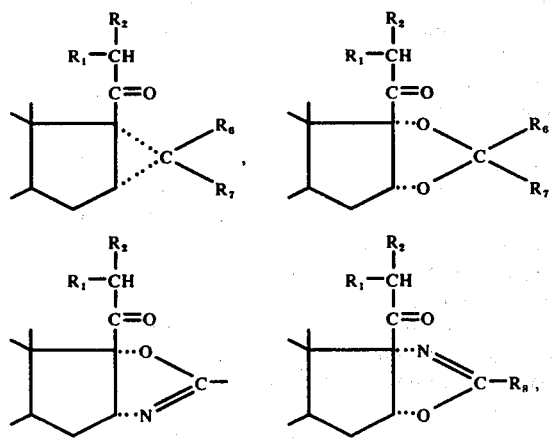

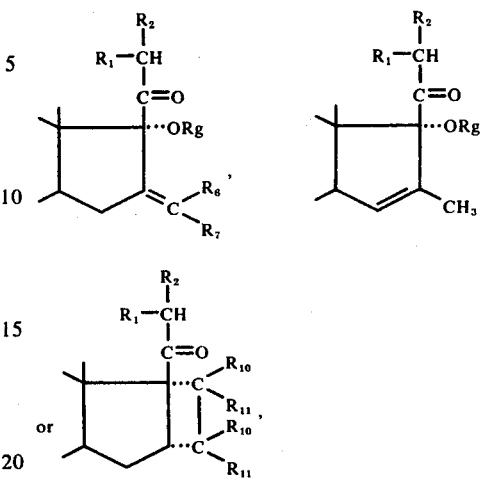

wherein $R_1$ and $R_2$ have the meanings given hereinbefore, $R_6$ = H or methyl, $R_7$ = H or methyl $R_8$ = H, methyl or phenyl, $R_9$ = H, alkyl or acyl, $R_{10}$ = H or halogen and $R_{11}$ = H, halogen or methyl.

Specific examples of compounds according to the invention are 11$\beta$-hydroxy-16$\alpha$,17$\alpha$-methylene-21-methyl-$\Delta^{1,4}$-pregnadiene-3,20-dione and its 9$\alpha$-fluoro-analogue; 11$\beta$-hydroxy-16$\alpha$,17$\alpha$-propylidenedioxy-21-methyl-$\Delta^{1,4}$-pregnadiene-3,20-dione and its 9$\alpha$-fluoro-analogue; 11$\beta$-hydroxy-[16$\alpha$,17$\alpha$-d]-2'-methyl-oxazoline-21-methyl-$\Delta^{1,4}$-pregnadiene-3,20-dione and its 9$\alpha$-fluoro-analogue; 9$\alpha$-fluoro-16$\alpha$,17$\alpha$-propylidenedioxy-21-methyl-$\Delta^{1,4}$-pregnadiene-3,11,20-trione; 9$\alpha$,11$\beta$-dichloro-16$\alpha$,17$\alpha$-propylidenedioxy-21-methyl-$\Delta^{1,4}$-pregnadiene-3,20-dione; 6$\alpha$-fluoro-16$\alpha$,17$\alpha$-propylidenedioxy-21-methyl-$\Delta^{1,4}$-pregnadiene-3,20-dione; 9$\alpha$-fluoro-[16$\alpha$,17$\alpha$-d]-2'-methyloxazoline-21-methyl-$\Delta^{1,4}$-pregnadiene-3,11,20-trione; 11$\beta$,17$\alpha$-dihydroxy-16,16-methylene-21-methyl-$\Delta^{1,4}$-pregnadiene-3,20-dione; 11$\beta$-hydroxy-[17$\alpha$,16$\alpha$-d]-2'-methyloxazoline-21-methyl-$\Delta^{1,4}$-pregnadiene-3,20-dione and its 9$\alpha$-fluoro-analogue; 11$\beta$-hydroxy-16$\alpha$,17$\alpha$-ethylene-21-methyl-$\Delta^{1,4}$-pregnadiene-3,20-dione and its 9$\alpha$-fluoro-analogue.

The novel compounds of the invention possess strong anti-inflammatory properties when applied locally and cause little or no systemic thymolytic, adrenolytic and salt-retaining effects, and thus show a marked dissociation of local from systemic action. Consequently, they are very useful in the treatment of inflammatory conditions especially those associated with the skin and allergic reactions. These compounds can be administered topically in the form of ointments, creams, lotions or sprays and suppositories or by injection for instance intraarticularly for the local treatment of inflammation, possibly in combination with other active ingredients.

The compounds of the invention may be prepared from $\Delta^{16}$-21-alkyl-20-oxo- or $\Delta^{16}$-21,21-dialkyl-20-oxo compounds of the pregnane series having the partial formula:

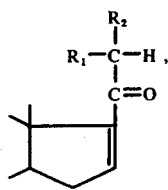

wherein R₁ and R₂ have the meanings given hereinbefore by introducing the substituents required at the positions 15, 16 and/or 17 of the end-products by methods known per se or from 20-oxo compounds of the pregnane series having the partial formula:

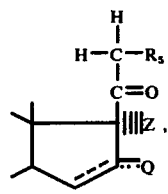

wherein Z and Q have the meanings given hereinbefore and R₅ = H or halogen, by 21-mono- or 21,21-dialkylation of these 20-oxo compounds according to the methods described in Belgian Pat. 793958 of Applicant (= South-Afr. Pat. 72/9103 = Dutch Pat. Appl. 7300313).

Other substituents indicated in the formula of the end-products may be introduced subsequently by methods known per se.

Starting from Δ¹⁶-20-oxo compounds as indicated above the various substituents in the 15-, 16- and/or 17-position may be introduced as follows:

A suitable Δ¹⁶-20-oxo compound is reacted for example with an appropriate diazo-compound in a suitable organic solvent such as ether or a halogenated hydrocarbon, and at a temperature preferably below 20° C to give a [17α,16α-c]-pyrazoline-20-oxo-steroid. By heat treatment, usually carried out at a temperature between 100° C and 250° C, possibly in an inert solvent such as decalin or toluene, or by acid treatment (e.g. perchloric acid, borontrifluoride or trifluoro acetic acid) of the pyrazolino compound nitrogen is split off, leaving a mixture of 16-alkyl-Δ¹⁶-20-oxo- and 16,17-alkylidene-20-oxo-steroids, their ratio to one another being dependent on the reaction conditions and the choice of the starting compound, i.e. the diazo-compound. The isomers can be separated by chromatography or crystallization.

A very convenient method for the preparation of 16,17-(substituted methylene)-20-oxo-steroids is the method described in the British Specification No. 1,235,285.

The 16-alkyl-Δ¹⁶-20-oxo compound is converted into the 16β-alkyl-16α,17α-epoxy-20-oxo compound by reaction with, for example, alkaline hydrogenperoxide, whereafter the epoxy compound is treated with an acid in a suitable solvent, e.g. HI in aqueous dioxan, p-toluene sulphonic acid in benzene, HBr in acetic acid, possibly followed by a reductive treatment which Raney nickel, so as to obtain the 16-alkylidene-17α-hydroxy-20-oxo-steroid, e.g. the 16-methylene-17α-hydroxy compound.

Besides or instead of the 16-alkylideen compound a Δ¹⁵-16-methyl-17α-hydroxy-20-oxo-steroid is obtained, dependent on the reaction conditions. In this connection reference is made to the methods described in British Specification No. 1,016,955. The isomers can be separated and/or purified by chromatography or crystallization.

The Δ¹⁶-20-oxo-steroid may be oxidised, e.g. by means of potassium permanganate in a buffered solution, to yield the 16α,17α-dihydroxy-20-oxo compound, which may be converted into the 16α,17α-alkylenedioxy-20-oxo-steroid by reaction with a ketone or an aldehyde, such as acetone, acetaldehyde, ethyl methyl ketone, propionaldehyde and the like. The reaction is allowed to take place in suspension or solution of the steroid in the ketone or aldehyde, with or without an inert organic solvent (e.g. dioxan) present, and in the presence of a mineral acid, e.g. HCl, HClO₄, p.TsOH (temp. between 15° and 60° C, reaction time 1–18 hrs). After the reaction the acid is neutralized and the product recovered.

Another route to the 16α,17α-alkylenedioxy-20-oxo-steroids is reacting the Δ¹⁶-20-oxo steroid with alkaline hydrogenperoxide in the presence of methanol to yield the 16α,17α-epoxy compounds, splitting open the 16α,17α-epoxy group by reaction with acetic acid and a hydrazine, e.g. H₂N.NHCO₂C₂H₅ and treating the 16α-acetoxy-17α-hydroxy-20-hydrazone compound obtained with pyruvic acid/acetic acid to obtain the 16α-acetoxy-17α-hydroxy-20-oxo compound, and finally reacting the 16α-acetoxy-17α-hydroxy-20-oxo compound with a ketone or an aldehyde, e.g. acetone or acetaldehyde, in an alcohol, e.g. methanol, in the presence of an acid, e.g. perchloric acid so as to obtain the 16α,17α-alkylene-dioxy-20-oxo-steroid.

A 16α,17α-ethylene- or 16α,17α-(substituted ethylene)-20-oxo-steroid may be obtained by reacting the Δ¹⁶-20-oxo-steroid with an olefin, e.g. ethylene or substituted ethylene, in an organic solution, e.g. benzene or dioxan, by the action of ultraviolet light (270–330 mµ) for 1–15 hours.

A [17α,16α-d]-oxazolino-20-oxo-steroid may be obtained as follows:

The Δ¹⁶-20-oxo-steroid is reacted in a solvent, e.g. tetrahydrofuran, with N-bromo-acetamide in the presence of HClO₄, preferably in the dark, or with saturated HBr/acetic acid to give the 17α-bromo-16β-hydroxy-20-one. This 20-ketone is converted into the 16α,17β-epoxy-20-one by treating with KOH in boiling methanol. The β-epoxide is reacted with sodium azide in methanol, containing H₂SO₄, under reflux to yield the 17α-azido-16α-hydroxy-20-one. For the preparation of the [17α,16α-d]-2'-methyl-oxazolino-20-oxo compound the 17α-azido-16α-hydroxy compound is converted into the 16α-acetate, e.g. by reaction with acetic anhydride/pyridine, whereafter the 17α-azido-16α-acetate is reduced, e.g. with PtO₂/H₂ in methanol, to give the [17α,16α-d]-2'-methyl-oxazoline-20-oxo-steroid.

The [16α,17α-d]-isomer may be prepared as follows:

The Δ¹⁶-20-oxo-steroid is reacted with alkaline hydrogenperoxide to give the 16α,17α-epoxy-20-oxo compound, which is reacted with sodium azide to obtain the 16β-azido-17α-hydroxy-20-one. Reaction of the last-mentioned compound with acetic anhydride/pyridine yields the corresponding 17α-acetate, which is reduced, for example with H₂/PtO₂ or H₂/Raney Ni, to the 16β-amino-17α-acetoxy-20-one. The 16β-amino-17α-acetoxy-20-one is converted into the corresponding 16β-chloramino compound by reaction with N-chlorosuccinimide in e.g. methylenechloride. Subsequent heating of the 16β-chloramino-17α-acetoxy- 20-one with potassium acetate in a solvent, e.g. dimethylformamide gives the 16-imino-17α-acetoxy-20-one, which is acetylated with acetic anhydride/acetic acid to obtain the $\Delta^{15}$-16-acetamido-17α-acetoxy-20-one. Subsequent base hydrolysis, e.g. with potassium carbonate/methanol affords the $\Delta^{15}$-16-acetamido-17α-hydroxy-20-one, which is reduced with $H_2$/Pd on charcoal to the 16α-acetamido-17α-hydroxy-20-one. Ring closure is effected by heating the latter with an acid, e.g. p-toluene sulphonic acid, to yield the [16α,17α-d]-2'-methyl-oxazolino-20-oxo steroid.

In all reactions described above reactive or vulnerable groups present elsewhere in the steroid molecule are protected according to methods known in the art.

Starting materials for the preparation of the compounds according to the invention can be 20-oxo-pregnanes of the formula:

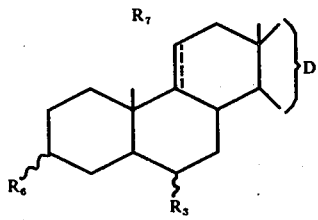

wherein
$R_3$ = H, $CH_3$ or halogen dotted lines indicate optional double bonds,
$R_6$ = a protected hydroxyl or keto group,
$R_7$ = hydrogen or a protected hydroxyl group, and D denotes the D-ring structure indicated by the partial formulae given hereinbefore.

During the alkylation procedure, it is preferable to protect an oxygen function at C-3 if one is present by reversible ether formation such as the tetrahydropyranyl ether in the case of a 3-hydroxyl group or a $\Delta^{3,5}$-enol ether in the case of a $\Delta^4$-3-keto grouping, or by ketal formation such as the dimethyl ketal in the case of a 3-keto group to prevent unwanted alkylation reactions such as O-alkylation which would take place at the same time as 21-alkylation if the starting material contained a free 3-hydroxyl group or 3-acyloxy group or to prevent unwanted C-alkylation reactions from taking place in the α-position to a free 3-keto group if such were present. It has been found that the 3-0-alkylated products which are formed if a free 3-hydroxyl group or its acyl derivative is present during the alkylation reaction are very difficult to hydrolyse back to the desired 3-hydroxyl group which is a necessary precursor for converting by oxidation to the 3-keto group in the final products according to the invention.

Similarly it is necessary to protect an 11-hydroxyl substituent if one is present in the starting material before carrying out the alkylation procedure to prevent the simulataneous formation of an 11-0-alkylated derivative which cannot be readily converted back to the free hydroxyl group. When an 11α-hydroxy-group is present, it is preferable to protect it by reversible ether formation such as the tetrahydropyranyl ether but when an 11β-hydroxyl substituent is present, because of its very sterically hindered position in the steroid molecule it is sufficient to protect it as an ester such as the acetate in which case the acyl group may itself undergo alkylation.

After introduction of the substituents required at the positions 15, 16 and/or 17 of the 21-alkyl or 21,21-dialkyl compounds by the methods described above or of the 21-alkyl or 21,21-dialkyl substituents into the 20-oxo compounds already carrying the 15-, 16- and/or 17-substituents, as indicated hereinbefore, other groups already present in the starting materials may be modified and new groups of functions may be introduced by methods known per se to furnish the desired end-products according to the invention.

A 3-hydroxyl group may be oxidised after hydrolysis of the protecting ether group, for example, by Oppenauer oxidation in the case of a $\Delta^5$-steroid to furnish a $\Delta^4$-3-keto-steroid, or with chromic acid in the case of either a 5α- or 5β-3-hydroxy derivative to give the corresponding saturated 3-ketone.

Where a 3-keto group in the starting material is protected as its ketal derivative, or in the case of a $66^4$-3-ketone, as the enol-ether for the purpose of the alkylation reaction, it is only necessary to hydrolyse it to regenerate the keto group.

In compounds containing a $\Delta^4$-3-keto grouping, additional double bonds may be introduced at positions $C_1$-$C_2$ and/or $C_6$-$C_7$ by known chemical means such as by reaction with suitable quinone derivatives or microbiologically with an appropriate micro-organism.

A 3-keto-5α-steroid may be converted to a $\Delta^{1,4}$-3-keto steroid by means of selenium dioxide or by reaction with a quinone such as dichlorodicyanobenzoquinone or by halogenation at positions 2 and 4 and subsequent dehydrohalogenation by methods known per se.

A 3-keto-5β-steroid may be converted into a $\Delta^4$-3-ketosteroid by means of selenium dioxide or by monobromination at position 4 followed by dehydrobromination and the so formed $\Delta^4$-3-ketone may be transformed into the $\Delta^{1,4}$-3-ketone by further reaction with selenium dioxide or dichlorodicyanobenzoquinone. Alternatively, a 3-keto-5β-steroid may be converted directly into a $\Delta^{1,4}$-3-ketone by reaction with selenium dioxide or by reaction with a suitable quinone such as dichlorodicyanobenzoquinone, or by di-halogenation for example di-bromination at positions 2 and 4 and subsequent dehydrohalogenation by methods known per se.

A $\Delta^4$-3-keto steroid may be converted into the corresponding $\Delta^6$-derivative by reaction with a suitable quinone such as chloranil and the thus formed $\Delta^{4,6}$-3-keto compound may then be converted to the corresponding $\Delta^{1,4,6}$-3-keto derivative by reaction with an appropriate quinone such as dichlorodicyanobenzoquinone.

The microbiological introduction of a double bond at position $C_1$-$C_2$ may be carried out by incubation with a 1,2-dehydrogenating micro-organism, for example *Corynbacterium simplex, Bacillus sphaericus* or *Bacillus subtilis*.

Introduction of a 6-substituent, if not already present may be effected if desired by converting a 3-hydroxy-$\Delta^5$-steroid into the 5α,6α-epoxide and treating the latter with methyl magnesium halide, a halogen acid, boron trifluoride or fluoroboric acid to give in each case the corresponding 5α-hydroxy-6β-substituted derivative which can then be converted into the corresponding $\Delta^4$-3-keto-6β-substituted compound by oxidising the 3-hydroxy group with, for example, chromic acid and dehydrating the 5-hydroxyl group appropriately under acid or basic conditions. Isomerisation of the 6β-substituent may be brought about by treatment with acid or base.

A $\Delta^{9(11)}$-double bond if present may be converted to the 9α-bromo-11β-hydroxy compound or an ester thereof by methods known per se and then transformed under basic conditions into a 9β,11β-epoxide which may be subsequently opened with a halogen acid to give the corresponding 9α-halo-11β-hydroxy derivative which can then be oxidised to the corresponding 9α-halo-11-ketone.

Introduction of an 11-hydroxyl group may be performed microbiologically, e.g. by incubation with an 11-hydroxylating micro-organism such as Curvularia or a Rhizopus after which the 11-hydroxyl group may be oxidised to an 11-keto group, acylated or dehydrated to form a $\Delta^{9(11)}$-double bond.

A $\Delta^{9(11)}$-double bond may be converted to a 9,11-dihalogen derivative such as the dichloride by addition of a halogen such as chlorine.

After elaboration of the $\Delta^{1,4}$-3-keto group an 11β-acyloxy group, if present, may be hydrolysed to the corresponding 11β-hydroxy derivative under relatively mild conditions with alcoholic alkali and the so formed 11β-hydroxy group may then be oxidized if desired to the corresponding ketone.

The acyloxy group present in the position 11 and/or 17 may be derived from a saturated or unsaturated organic carboxylic acid having 1–18 carbon atoms and is preferably a lower alkanoyloxy group, such as acetyloxy, propionyloxy, valerianyloxy and the like.

The 21-alkylated compounds according to the invention are very active in the "human vasoconstriction" test, indicating their good to excellent potency as antiinflammatories. They have the further advantage over the known 21-desmethyl compounds that they are more soluble in the usual vehicles for topical application.

The invention is further illustrated by the following examples.

EXAMPLE 1 a. To a stirred suspension of 3β-hydroxy-$\Delta^{9(11),16}$-5α-pregnadien-20-one in sodium-dried benzene was added excess dihydropyran and a catalytic quantity of p-toluenesulphonic acid. After 1 hour the solution was washed with sodium carbonate solution, then to neutrality with water, dried and evaporated to a gummy solid, which was crystallised from petroleum ether to give 3β-hydroxy-$\Delta^{9(11),16}$-5α-pregnadien-20-one 3-tetrahydropyranyl ether.

b. To a stirred solution of lithium diisopropylamide in sodium-dried tetrahydrofuran under nitrogen at 0° C was added a solution of 3β-hydroxy-$\Delta^{9(11),16}$-5α-pregnadien-20-one 3-tetrahydropyranyl ether (0.66 mole equivalents) in sodium-dried tetrahydrofuran. After the solution had been stirred for 30 minutes at room temperature, external cooling was again applied and excess dry methyl iodide was added. The cooling bath was removed, and after 45 minutes the solvent was evaporated under vacuum. The residue was dissolved in aqueous acetic acid and after 4 hours the product was precipitated by the addition of water. Crystallisation from acetone/hexane gave 3β-hydroxy-21-methyl-$\Delta^{9(11),16}$-5α-pregnadien-20-one.

c. To a stirred solution of lithium diisopropylamide in dry tetrahydrofuran under nitrogen at 0° C was added a solution of 3β-hydroxy-21-methyl-$\Delta^{9(11),16}$-5α-pregnadien-20-one 3-tetrahydropyranyl ether (0.66 mole equivalents) in dry tetrahydrofuran. After the solution had been stirred for 30 minutes at room temperature, external cooling was again applied and excess dry methyl iodide was added. The cooling bath was removed, and after 45 minutes the solvent was evaporated under vacuum. The residue was dissolved in aqueous acetic acid and the solution allowed to stand overnight. The product was precipitated by the addition of water, filtered, dried and crystallised from acetone/hexane to give 3β-hydroxy-21,21-dimethyl-$\Delta^{9(11),16}$-5α-pregnadien-20-one.

d. To a solution of 3β-hydroxy-21-methyl-$\Delta^{9(11),16}$-5α-pregnadien-20-one (9.97 g) in methylene chloride and methanol was added 4N sodium hydroxide (20 ml) followed by 30% hyrogen peroxide (20 ml). The reaction mixture was shielded from light and allowed to stand overnight. External cooling was applied and sodium sulphite solution was added to decompose excess hydrogen peroxide. The methylene chloride was then evaporated under vacuum and the reaction mixture was poured into water. Filtration of the solid gave 3β-hydroxy-16α,17α-epoxy-21-methyl-$\Delta^{9(11)}$-5α-pregnen-20-one. In a similar manner 3β-hydroxy-21,21-dimethyl-$\Delta^{9(11),16}$-5α-pregnadien-20-one was converted to 3β-hydroxy-16α,17α-epoxy-21,21-dimethyl-$\Delta^{9(11)}$-5α-pregnen-20-one.

e. To a stirred solution of 3β-hydroxy-16α,17α-epoxy-21-methyl-$\Delta^{9(11)}$-5α-pregnen-20-one (9.5 g) in acetic acid was added a solution of carbethoxy hydrazine (9.5 g) in acetic acid. The reaction mixture was stirred overnight then poured into ice-water. Filtration gave 3β,16α,17α-trihydroxy-21-methyl-$\Delta^{9(11)}$-5α-pregnen-20-one 16-acetate 20-carbethoxy hydrazone.

In a similar manner 3β-hydroxy-16α,17α-epoxy-21,21-dimethyl-$\Delta^{9(11)}$-5α-pregnen-20-one was converted to 3β,16α,17α-trihydroxy-21,21-dimethyl-$\Delta^{9(11)}$-5α-pregnen-20-one 16-acetate 20-carbethoxy hydrazone.

f. 3β,16α,17α-Trihydroxy-21-methyl-$\Delta^{9(11)}$-5α-pregnen-20-one 16-acetate 20-carbethoxy hydrazone (13.3 g) was dissolved in acetic acid at 100° C and 50% aqueous pyruvic acid (13.3 ml) was added. After 10 minutes at 100° C water was slowly added for a further 20 minutes after which the solution was allowed to cool and with the continued slow addition of water. The solid was filtered to give 3β,16α,17α-trihydroxy-21-methyl-$\Delta^{9(11)}$-5α-pregnen-20-one 16-acetate.

In a similar way 3β,16α,17α-trihydroxy-21,21-dimethyl-$\Delta^{9(11)}$-5α-pregnen-20-one 16-acetate 20-carbethoxy hydrazone was converted to 3β,16α,17α-trihydroxy-21,21-dimethyl-$\Delta^{9(11)}$-5α-pregnen-20-one 16-acetate.

g. To a solution of 3β,16α,17α-trihydroxy-21-methyl-$\Delta^{9(11)}$-5α-pregnen-20-one 16-acetate (7.5 g) in acetone and methanol was added 70% perchloric acid (7.5 ml) and the solution was heated to reflux for 1 hour, then cooled and poured into water containing sodium acetate. Filtration of the product gave 3β-hydroxy-16α,17α-isopropylidenedioxy-21-methyl-$\Delta^{9(11)}$-5α-pregnen-20-one. In a similar way 3β,16α,17α-trihydroxy-21,21-dimethyl-$\Delta^{9(11)}$-5α-pregnen-20-one 16-acetate was converted to 3β-hydroxy-16α,17α-isopropylidenedioxy-21,21-dimethyl-$\Delta^{9(11)}$-5α-pregnen-20-one.

h. 3β-Hydroxy-16α,17α-isopropylidenedioxy-21-methyl-$\Delta^{9(11)}$-5α-pregnen-20-one was dissolved in acetone and the stirred solution was cooled in an ice bath. 6.24 N Jones Reagent was added dropwise until excess was present, and after the addition of a little isopropanol to decompose the excess, the solution was poured into water. The product was filtered off and purified by chromatography on silicagel and elution with mixtures of toluene/ethyl acetate. Crystallisation of the appropriate fractions from ether/hexane gave 16α,17α-isopropylidenedioxy-21-methyl-$\Delta^{9(11)}$-5α-pregnene-3,20-dione.

In a similar way 3β-hydroxy-16α,17α-isopropylidenedioxy-21,21-dimethyl-66$^{9(11)}$-5α-pregnen-20-one was converted to 16α,17α-isoproylidenedioxy-21,21-dimethyl-$\Delta^{9(11)}$-5α-pregnene-3,20-dione.

i. A solution of 16α,17α-isopropylidenedixoy-21-methyl-$\Delta^{9(11)}$-5α-pregnene-3,20-dione and dichlorodicyanobenzoquinone (2.4 mole equivalents) in toluene/acetic acid 10:1 was heated to reflux with stirring overnight. The cooled reaction mixture was filtered, then the filtrate was evaporated to dryness and the residue purged three times with toluene to remove acetic acid. The residue was then dissolved in toluene and the solution passed through a column of grade H alumina. Elution with ether and evaporation of the eluant gave the crude product. This was purified by chromatography on silicagel, with toluene/ethyl acetate mixture. The appropriate fractions were combined and crystallised from methylene chloride/methanol to give 16α,17α-isopropylidenedioxy-21-methyl-$\Delta^{1,4,9(11)}$-pregnatriene-3,20-dione.

In a similar manner 16α,17α-isopropylidenedioxy-21,21-dimethyl-$\Delta^{9(11)}$-5α -pregnene-3,20-dione was converted to 16α,17α-isopropylidenedioxy-21,21-dimethyl-$\Delta^{1,4,9(11)}$-pregnatriene-3,20-dione.

j. To a stirred solution of 16α,17α-isopropylidenedioxy-21-methyl-$\Delta^{1,4,9(11)}$-pregnatriene-3,20-dione (2 g) in tetrahydrofuran was slowly added 0.5 N perchloric acid (10 ml) followed by N-bromoacetamide (1 g) with exclusion of light. After 30 minutes, sodium sulphite solution was added and the reaction mixture was poured into water. Filteration of the solid gave 9α-bromo-11β-hydroxy-16α,17α-isopropylidenedioxy-21-methyl-$\Delta^{1,4}$-pregnadiene-3,20-dione.

In s similar manner 16α,17α-isopropylidenedioxy-21,21-dimethyl-$\Delta^{1,4,9(11)}$-pregnatriene-3,20-dione was converted to 9α-bromo-11β-hydroxy-16α,17α-isopropylidenedioxy-21,21-dimethyl-$\Delta^{1,4}$-pregnadiene-3,20-dione.

k. To a stirred solution of n-butane thiol (3.6 ml) in dimethyl sulphoxide under oxygen-free nitrogen was added freshly prepared chromous acetate (4.74 g), followed by a solution of crude 9α-bromo-11β-hydroxy-16α,17α-isopropylidenedioxy-21-methyl-$\Delta^{1,4}$-pregnadiene-3,20-dione (2.37 g) in dimethyl sulphoxide. The reaction flask was stoppered and the solution stirred magnetically overnight.

The mixture was then poured into saturated sodium chloride solution and the product extracted into ethyl acetate. The solution was washed with 5% sodium carbonate solution, then to neutrality with water, dried and evaporated to dryness. Crystallisation of the residue from methylene chloride/methanol gave 11β-hydroxy-16α,17α-isopropylidenedioxy-21-methyl-$\Delta^{1,4}$-pregnadiene-3,20-dione. M.p. 286°–306° C. In a similar manner 9α-bromo-11β-hydroxy-16α,17α-isopropylidenedioxy-21,21-dimethyl-$\Delta^{1,4}$-pregnadiene-3,20-dione was converted to 11β-hydroxy-16α,17α-isopropylidenedioxy-21,21-dimethyl-$\Delta^{1,4}$-pregnadiene-3,20-dione. M.p. 265°–271° C.

EXAMPLE 2 a. A suspension of 3β-hydroxy-16α,17α-epoxy-21-methyl-$\Delta^{9(11)}$-5α-pregnen-20-one in aqueous dimethyl sulphoxide was treated with sodium azide and conc. $H_2SO_4$ and stirred under reflux for 2 hours. The reaction mixture was cooled, poured into water and the solid product was filtered and dried. The crude diol was suspended in glacial acetic acid and acetic anhydride, and the mixture was warmed in a hot water bath for 15 minutes with a catalytic quantity of p-toluene sulphonic acid. The resultant solution was poured onto ice-chips, allowed to attain room temperature and the brown solid filtered and dried. Crystallisation from methylene chloride/methanol gave pure 3β,17α-dihydroxy-16β-azido-21-methyl-$\Delta^{9(11)}$-5α-pregnen-20-one-3,17-diacetate.

In a similar way the corresponding 21,21-dimethyl epoxide gave 3β,17α-dihydroxy-16β-azido-21,21-dimethyl-$\Delta^{9(11)}$-5α-pregnen-20-one 3,17-diacetate.

b. A mixture of 3β,17α-dihydroxy-16β-azido-21-methyl-$\Delta^{9(11)}$-5α-pregnen-20-one 3,17-diacetate, in acetic acid and platinum oxide was shaken in an atmosphere of hydrogen for 4 hours. The catalyst was filtered off and the filtrate evaporated to low volume, diluted with water and extracted with ether. The extract was washed with 2N HCl and the acid extracts basified to give a solid which was filtered and dried to yield pure 3β,17α-dihydroxy-16β-amino-21-methyl-$\Delta^{9(11)}$-5α-pregnen-20-one 3,17-diacetate. In a similar manner the 21,21-dimethyl-16β-azide was converted to the corresponding amine.

c. A mixture of 3β,17α-dihydroxy-16β-amino-21-methyl-$\Delta^{9(11)}$-5α-pregnen-20-one diacetate, methylene chloride and N-chlorosuccinimide was stirred at room temperature for 60 minutes then diluted with water. The organic layer was separated, dried and evaporated and the residue crystallised from ether/n-hexane to give 3β,17α-dihydroxy-16β-chloramino-21-methyl-$\Delta^{9(11)}$-5α-pregnen-20-one diacetate.

The chloramine was suspended in dimethyl formamide, solid potassium acetate was added and the mixture stirred for 60 minutes at 40° C under nitrogen. The reaction mixture was cooled, diluted with water and the resultant solid filtered and dried. Crystallisation from acetone/n-hexane gave 3β,17α-dihydroxy-16-imino-21-methyl-$\Delta^{9(11)}$-pregnen-20-one diacetate.

In a similar manner, treatment of the 16β-amino-21,21-dimethyl-pregnane under the same conditions yielded 3β,17α-dihyroxy-16-imino-21,21-dimethyl-$\Delta^{9(11)}$-5α-pregnen-20-one diacetate.

d. A suspension of 3β,17α-dihydroxy-16-imino-21-methyl-$\Delta^{9(11)}$-5α-pregnen-20-one diacetate in 95:5 acetic acid: acetic anhydride was stirred for 30 minutes at room temperature, then diluted with water and the resultant white solid was filtered and dried to give 3β,17α-dihydroxy-16-acetamide-21-methyl-$\Delta^{9(11),15}$-pregnadien-20-one diacetate. The crude acetamide was suspended in methanolic potassium carbonate and the mixture stirred at room temperature. After 3 hours the solution was poured into water and the white solid filtered and dried to yield 3β,17α-dihydroxy-16-acetamido-21-methyl-$\Delta^{9(11),15}$-pregnadien-20-one. The crude diol was dissolved in 1:1 pyridine:acetic anhydride and left for 3 hours at room temperature. The solution was poured into crushed ice, allowed to attain room temperature before the solid was filtered and dried. Crystallisation from methylene chloride/methanol yielded pure 3β,17α-dihydroxy-16-acetamido-21-methyl-Δ$^{9(11),15}$-pregnadien-20-one 3-acetate. This acetamide was dissolved in acetic acid, and the mixture hydrogenated for 5 hours in the presence of platinum oxide catalyst. The catalyst was removed by filtration, the acetic acid was evaporated and the residue dissolved in ethyl acetate, washed, dried and evaporated to give the product as a crystalline mass. Recrystallisation from methylene chloride/methanol gave pure 3β,17α-dihydroxy-16α-acetamido-21-methyl-Δ$^{9(11)}$-5α-pregnen-20-one 3-acetate.

Treatment of 3β,17α-dihydroxy-16-imino-21,21-dimethyl-Δ$^{9(11),15}$-pregnadien-3,20-dione, 3,17-diacetate under the same reaction conditions yielded 3β,17α-dihydroxy-16α-acetamido-21,21-dimethyl-Δ$^{9(11)}$-5α-pregnen-20-one 3-acetate.

e. A mixture of 3β,17α-dihydroxy-16α-acetamido-21-methyl-Δ$^{9(11)}$-5α-pregnen-20-one 3-acetate and methanolic potassium carbonate was stirred for 4 hours then poured into water. The white solid was filtered and dried to give 3β,17α-dihydroxy-16α-acetamido-21-methyl-Δ$^{9(11)}$-5α-pregnen-20-one. The diol was suspended in acetone and treated with 8N chromic acid at 0°. After 10 minutes the mixture was treated with isopropanol then diluted to five volumes of water. The product was extracted into ethylacetate, dried and evaporated to give 16α-acetamido-17α-hydroxy-21-methyl-Δ$^{9(11)}$-5α-pregnene-3,20-dione as a gum. The crude dione was dissolved in dry benzene, p-toluene sulphonic acid was added and the mixture stirred under reflux. After 30 minutes the reaction was cooled and washed with potassium bicarbonate solution and water, then dried and evaporated to give a crystalline mass. Crystallisation from acetone/n-hexane gave pure [16α,17α-d]-2'-methyl-oxazoline-21-methyl-Δ$^{9(11)}$-5α-pregnene-3,20-dione. Treatment of 3β,17α-dihydroxy-16α-acetamido-21,21-dimethyl-Δ$^{9(11)}$-pregnen-20-one 3-acetate under the same conditions furnished [16α,17α-d]-2'-methyl oxazoline-21,21-dimethyl-Δ$^{9(11)}$-5α-pregnene-3,20-dione.

f. A solution of bromine in dioxan was added dropwise to a stirred solution of [16α,17α-d]-2'-methyloxazoline-21-methyl-Δ$^{9(11)}$-5α-pregnene-3,20-dione in dioxan containing a little hydrogen bromide/acetic acid solution. After 1 hour the reaction was poured into an ice-cold sodium carbonate solution and the product filtered and dried.

The crude 2,4-dibromo derivative in dimethyl-acetamide was added to a mixture of lithium bromide, lithium carbonate in dimethyl-acetamide, stirred and heated at 100° C under a nitrogen atmosphere. After 12 hours the mixture was cooled, poured into sodium chloride solution and treated with acetic acid. The solid product was filtered, dried and purified by chromatography to give [16α,17α-d]-2'-methyl-oxazoline-21-methyl-Δ$^{1,4,9(11)}$-pregnatriene-3,20-dione.

Treatment of [16α,17α-d]-2'-methyl-oxazoline-21,21-dimethyl-Δ$^{9(11)}$-5α-pregnene-3,20-dione in the above manner yielded the corresponding [16α,17α-d]-2'-methyl-oxazoline-21,21-dimethyl-Δ$^{1,4,9(11)}$-5α-pregnatriene-3,20-dione.

g. A solution of [16α,17α-d]-2'-methyloxazoline-21-methyl-Δ$^{1,4,9(11)}$-pregnatriene-3,20-dione in tetrahydrofuran was treated with 0.5 N perchloric acid and N-bromo acetamide, then the resultant mixture was stirred in the dark. After 1 hour the solution was treated with sodium bisulphite diluted with water and the white precipitate filtered and dried to yield 9α-bromo-11β-hydroxy-[16α,17α-d]-2'-methyl-oxazoline-21-methyl-Δ$^{1,4}$-pregnadiene-3,20-dione.

Treatment of [16α,17α-d]-2'-methyloxazoline-21,21-dimethyl-Δ$^{1,4,9(11)}$-pregnatriene-3,20-dione under the same conditions furnished 9α-bromo-11β-hydroxy-[16α,17α-d]-2'-methyloxazoline-21,21-dimethyl-Δ$^{1,4}$-pregnadiene-3,20-dione.

h. n-Butane thiol was added to a stirred solution of dimethyl sulphoxide under "oxygen-free" nitrogen. Freshly prepared chromous acetate was then added in one portion followed by a solution of 9α-bromo-11β-hydroxy-[16α,17α-d]-2'-methyloxazoline-21-methyl-Δ$^{1,4}$-pregnadiene-3,20-dione. After 5 hours the reaction mixture was poured into a saturated sodium chloride solution, extracted with ethyl acetate and the organic extract washed with sodium carbonate, water, dried and evaporated. Crystallisation of the crude yielded pure 11β-hydroxy-[16α,17α-d]-2'-methyloxazoline-21-methyl-Δ$^{1,4}$-pregnadiene-3,20-dione. M.P. 263°–270° C.

Treatment of the corresponding 21,21-dimethyl bromohydrin under the same conditions furnished 11β-hydroxy-[16α,17α-d]-2'-methyloxazoline-21,21-dimethyl-Δ$^{1,4}$-pregnadiene-3,20dione. M.p. 202°–208° C.

EXAMPLE 3 a. A solution of 3β,11β-dihydroxy-21-methyl-Δ$^{16}$-5α-pregnen-20-one 3β,11β-diacetate in methylene chloride was added to an ice-cold solution of excess diazomethane in ether. The solution was allowed to stand in a refrigerator for 4 days, then excess diazomethane was destroyed by the addition of a 10% solution of acetic acid in ether. The solution was evaporated to dryness and purged with toluene to remove acetic acid.

The product was dissolved in dimethyl formamide and the solution was heated to reflux with stirring for one hour, then cooled and poured into water. The solid product was filtered, dried and crystallised from acetone/ether to give 3β,11β-dihydroxy-16,21-dimethyl-Δ$^{15}$-5α-pregnen-20-one 3β,11β-diacetate. Treatment of 3β,11β-dihydroxy-21,21-dimethyl-Δ$^{16}$-5α-pregnen-20-one 3β,11β-diacetate in a similar manner gave 3β,11β-dihydroxy-16,21,21-trimethyl-Δ$^{16}$-5α-pregnen-20-one.

b. To a solution of 3β,11β-dihydroxy-16,21-dimethyl-Δ$^{16}$-5α-pregnen-20-one 3β,11β-diacetate (10 g) in methylene chloride and methanol was added 4N sodium hydroxide solution (20 ml) and 30% hydrogen peroxide solution (20 ml). Light was excluded and the reaction mixture immersed in a constant temperature bath at 40° C. Further 30% hydrogen peroxide solution (5 ml) was added after 18 hours and again after 25 hours. After 41 hours the reaction mixture was cooled in ice and sodium sulphite solution added. The methylene chloride was removed under reduced pressure and the mixture was poured into water. The solid product was filtered and dried to give 3β,11β-dihydroxy-16β,21-dimethyl-16α,17α-epoxy-5α-pregnan-20-one 11β-acetate.

In a similar manner 3β,11β-dihydroxy-16,21,21-trimethyl-Δ$^{16}$-5α-pregnen-20-one 3β,11β-diacetate was converted to 3β,11β-dihydroxy-16β,21,21-trimethyl-16α,17α-epoxy-5α-pregnan-20-one 11β-acetate.

c. A solution of 3β,11β-dihydroxy-16β,21-dimethyl-16α,17α-epoxy-5α-pregnan-20-one 11β-acetate (10 g) in tetrahydrofuran was treated with hydrogen bromide in acetic acid (3.1% w/v; 10 ml) and the solution was allowed to stand at room temperature. After 2 hours the solution was poured into dilute aqueous sodium acetate. The solid product was filtered, dried and crystallised from acetone/ether to give 3β,11β,17α-trihydroxy-16,16-methylene-21-methyl-5α-pregnan-20-one 11β-acetate.

Treatment of 3β,11β-dihydroxy-16,21,21-trimethyl-16α,17α-epoxy-5α-pregnan-20-one 11β-acetate in a similar manner gave 3β,11β,17α-trihydroxy-16,16-methylene-21,21-dimethyl-5α-pregnan-20-one 11β-qcetate.

d. In the manner as described in the Examples 1 (h) and (i) 3β,11β,17α-trihydroxy-16,16-methylene-21-methyl-5α-pregnan-20-one 11β-acetate and β,11β,,17α-trihydroxy-16,16-methylene-21,21-dimethyl-5α-pregnan-20-one 11β-acetate were converted to 11β,17α-dihydroxy-16,16-methylene-21-methyl-$\Delta^{1,4}$-pregnadiene-3,20-dione 11β-acetate (m.p. 184°–189° C) and 11β, 17α-dihydroxy-16,16-methylene-21,21-dimethyl-$\Delta^{1,4}$-pregnadiene-3,20-dione 11β-acetate (m.p. 172°–175° C), respectively.

e. A solution of 11β,17α-dihydroxy-16,16-methylene-21-methyl-$\Delta^{1,4}$-pregnadiene-3,20-dione 11β-acetate in methanol was treated with a large excess of 10N potassium hydroxide solution and the mixture stirred overnight under nitrogen. The mixture was then neutralised with acetic acid, and poured into water. The solid product was filtered, dried and crystallised from methylene chloride/methanol to give 11β,17α-dihydroxy-16,16-methylene-21-methyl-$\Delta^{1,4}$-pregnadiene-3,20-dione, m.p. 191°–195° C.

In a similar manner 11β,17α-dihydroxy-16,16-methylene-21,21-dimethyl-$\Delta^{1,4}$-pregnadiene-3,20-dione 11β-acetate was converted to 11β,17α-dihydroxy-16,16-methylene-21,21-dimethyl-$\Delta^{1,4}$-pregnadiene-3,20-dione, m.p. 180°–185° C.

EXAMPLE 4 a. A suspension of 3β,11β-dihydroxy-$\Delta^{16}$-5α-pregnen-20-one (50 g) in dry benzene (750 ml) was treated with dihydropyran (50 ml) and p-toluene sulphonic acid (2 g). After 1 hour the mixture was washed with 5% sodium carbonate solution then with water, dried and filtered. The filtrate was evaporated to give 3β,11β-dihydroxy-$\Delta^{16}$-5α-pregnen-20-one, 3,11-ditetrahydropyranyl ether as an oil (97 g).

The crude ditetrahydropyranyl ether (97 g) in cold tetrahydrofuran (1,250 ml) was added to a solution of lithium diisopropylamide in tetrahydrofuran at 0° C, the mixture stirred for 30 minutes at room temperature, then re-cooled and treated with methyl iodide (250 ml). After 10 minutes the mixture was evaporated in vacuo and the residue dissolved in acetic acid (250 ml) and water (100 ml), warmed on a steam bath for 30 minutes, cooled, diluted to 3 liters with water and the resultant solid filtered and dried. Crystallisation from ethyl acetate gave 3β,11β-dihydroxy-21-methyl-$\Delta^{16}$-5α-pregnen-20-one.

In a similar manner 3β,11β-dihydroxy-21-methyl-$\Delta^{16}$-5α-pregnen-20-one was converted via its 3,11-ditetrahydropyranyl ether to 3β,11β-dihydroxy-21,21-dimethyl-$\Delta^{16}$-5α-pregnen-20-one.

b. A mixture of 3β,11β-dihydroxy-21-methyl-$\Delta^{16}$-5α-pregnen-20-one (40 g), acetic anhydride (160 ml) and pyridine (80 ml) was treated at reflux for 7 hours. Methylamine hydrochloride (0.8 g) was then added and the heating continued for a further 3 hours. The resultant mixture was cooled, poured onto crushed ice, allowed to reach room temperature and the brown solid filtered and dried. Crystallisation from diethyl ether gave 3β,11β-dihydroxy-21-methyl-$\Delta^{16}$-5α-pregnen-20-one diacetate.

In a similar manner 3β,11β-dihydroxy-21,21-dimethyl-$\Delta^{16}$-5α-pregnen-20-one furnished the corresponding diacetate.

c. A mixture of 3β,11β-dihydroxy-21-methyl-$\Delta^{16}$-5α-pregnen-20-one 3,11-diacetate (24 g), N-bromosuccinimide (11.9 g), dimethyl formamide (240 ml) and perchloric acid (70%, 6.6 ml) was stirred in the dark at 10° C. After 24 hours the excess N-bromosuccinimide was destroyed with aqueous sodium bisulphite and the mixture poured into water (1200 ml). The product was filtered and dried at room temperature to give 3β,11β,16β-trihydroxy-17α-bromo-21-methyl-5α-pregnan-20-one 3,11-diacetate 16-formate. The crude formate (30 g) in methanolic potassium carbonate (400 ml) was stirred at room temperature for 2 hours. The excess base was neutralised with acetic acid, the reaction mixture concentrated in vacuo, poured into water and extracted with ether. The organic extract was washed, dried, and filtrate evaporated to give 3β,11β.dihydroxy-16β,17β-epoxy-21-methyl-5α-pregnan-20-one 11-acetate as an amorphous solid. Treatment of 3β,11β-dihydroxy-21,21-dimethyl-66$^{16}$-5α-pregnen-20-one 3,11-diacetate in a similar manner gave 3β,11β-dihydroxy-16β,17β-epoxy-21,21-dimethyl-5α-pregnan-20-one-11-acetate (amorphous).

d. A mixture of 3β,11β-dihydroxy-16β,17β-epoxy-21-methyl-5α-pregnan-20-one 11-acetate (40 g), sodium azide (120 g), ethanol (600 ml), water (300 ml) and sulphuric acid (8.4 ml) was stirred at reflux for 10 hours, cooled, and poured into water (1800 ml) and the resulting solid filtered and dried. The product was purified on silica gel to give 3β,11β,16α-trihydroxy-17α-azido-21-methyl-5α-pregnan-20-one 11-acetate.

A mixture of 3β,11β,16α-trihydroxy-17α-azido-21-methyl-5α-pregnan-20-one 11-acetate (6.3 g), pyridine (19 ml) and acetic anhydride (13 ml) was allowed to stand at room temperature for 16 hours. The solution was then poured into washed ice, allowed to reach room temperature and the white solid filtered and dried to give 3β,11β,16α-trihydroxy-17α-azido-21-methyl-5α-pregnan-20-one, 3,11,16-triacetate.

Treatment of 3β,11β-dihydroxy-16β,17β-epoxy-21,21-dimethyl-5α-pregnan-20-one 11-acetate in a similar manner gave 3β,11β,16α-trihydroxy-17α-azido-21,21-dimethyl-5α-pregnan-20-one 3,11,16-triacetate.

e. A mixture of 3β,11β,16α-trihydroxy-17α-azido-21-methyl-5α-pregnan-20-one 3,11,16-triacetate (5.1 g) and platinum oxide (0.5 g) in methanol (300 ml) was hydrogenated for 2 hours then filtered. The filtrate was evaporated to dryness to give 3β,11β,16α-trihydroxy-17α-amino-21-methyl-5α-pregnan-20-one 3,11,16-triacetate which was suspended in dry benzene (250 ml) in the presence of p-toluene-sulphonic acid (2.5 g). The reaction mixture was stirred at reflux for 1.5 hours then cooled and washed with 5% sodium carbonate, water, dried over magnesium sulphate, filtered, and the filtrate evaporated to dryness. Crystallisation from acetone/n-hexane furnished 3β,11β-dihydroxy-[17α,16α-d]-2'-methyloxazoline-21-methyl-5α-pregnan-20-one, 3,11-diacetate.

Treatment of 3β,11β,16α-trihydroxy-17α-azido-21,21-dimethyl-5α-pregnan-20-one 3,11,16-triaceate in a similar manner gave 3β,11β-dihydroxy-[17α,16- d]-2'-methyloxazoline-21,21-dimethyl-5α-pregnan-20-one 3,11-diacetate.

f. A suspension of 3β,11β-dihydroxy-[17α,16α-d]-2'-methyloxazoline-21-methyl-5α-pregnan-20-one 3,11-diacetate (3.5 g) in methanolic potassium carbonate (100 ml) was stirred at room temperature for 90 minutes then poured into water (500 ml) and extracted with ether. The organic extract was washed, dried, and evaporated to give 3β,11β-dihydroxy-[17α,16α-d]-2'-methyloxazoline-21-methyl-5α-pregnan-20-one 11-acetate.

Treatment of 21,21-dimethyl analogue in a similar manner gave 3β,11β-dihydroxy-[17α,16α-d]-2'-methyloxazoline-21,21-dimethyl-5α-pregnan-20-one 11-acetate.

g. In the manner as described in Example 1 h) 3β,11β-dihydroxy-[17α,16α-d]-2'-methyloxazoline-21-methyl-5α-pregnan-20-one 11-acetate (8 g) was converted to 11β-hydroxy-[17α,16α-d]-2'-methyloxazoline-21-methyl-5α-pregnane-3,20-dione 11-acetate.

Treatment of 3β,11β-dihydroxy-[17α,16α-d]-2'-methyloxazoline-21,21-dimethyl-5α-pregnan-20-one 11-acetate in a similar manner gave 11β-hydroxy-[17α,16α-d]-2'-methyloxazoline-21,21-dimethyl-5α-pregnane-3,20-dione 11-acetate.

h. In the manner as described in Example 2 (f) 11β-hydroxy-[17α,16α-d]-2'-methyloxazoline-21-methyl-5α-pregnane-3,20-dione 11-acetate (20 g) was converted via the 2,4-dibromo derivative to 11β-hydroxy-[17α,16α-d]-2'-methyloxazoline-21-methyl-$\Delta^{1,4}$-pregnadiene-3,20-dione 11-acetate m.p. 157°–168° C.

Treatment of 11β-hydroxy-[17α,16α-d]-2'-methyloxazoline-21,21-dimethyl-5α-pregnane-3,20-dione in a similar manner gave 11β-hydroxy-[17α,16α-d]-2'-methyloxazoline-21,21-dimethyl-$\Delta^{1,4}$-pregnadiene-3,20-dione 11-acetate m.p. 212°–214° C.

i. A solution of 11β-hydroxy-[17α,16α-d]-2'-methyloxazoline-21-methyl-$\Delta^{1,4}$-pregnadiene-3,20-dione 11-acetate (23.6 g) in methanol (472 ml) and 10N potassium hydroxide (94.4 ml) was heated at reflux. After 30 minutes the cooled reaction mixture was neutralised with acetic acid, the methanol distilled off in vacuo and the product filtered.

Crystallisation from ethyl acetate gave 11β-hydroxy-[17α,16α-d]-2'-methyloxazoline-21-methyl-$\Delta^{1,4}$-pregnadiene-3,20-dione m.p. 256°–258° C.

Treatment of 11β-hydroxy-[17α,16α-d]-2'-methyloxazoline-21,21-dimethyl-$\Delta^{1,4}$-pregnadiene-3,20-dione 11-acetate in a similar manner gave 11β-hydroxy-[17α,16α-d]-2'-methyloxazoline-21,21-dimethyl-$\Delta^{1,4}$-pregnadiene-3,20-dione, m.p. 258°–265° C.

EXAMPLE 5 a. A mixture of 3β-hydroxy-[17α,16α-d]-2'-methyloxazoline-$\Delta^{9(11)}$-5α-pregnen-20-one (10 g), dry benzene (150 ml), dihydropyran (10 ml) and p-toluene sulphonic acid (5 g) was stirred at room temperature. After 2 hours the solution was washed with sodium carbonate, water, dried over magnesium sulphate then filtered. The filtrate was evaporated to give 3β-hydroxy-[17α,16α-d]-2'-methyloxazoline-$\Delta^{9(11)}$-5α-pregnen-20-one 3-tetrahydropyranyl ether (15 g). This product was alkylated with lithium diisopropylamide as described in Example 4 a), deprotected then purified by chromatography on silica gel to give 3β-hydroxy-[17α,16α-d]-2'methyloxazoline-21-methyl-$\Delta^{9(11)}$-5α-pregnen-20-one.

b. By the method of the Examples 1(h) and (i) 3β-hydroxy-[17α,16α-d]-2'-methyloxazoline-21-methyl-$\Delta^{9(11)}$-5α-pregnen-20-one was converted via [17α,16α-d]-2'-methyloxazoline-21-methyl-$\Delta^{9(11)}$-5α-pregnene-3,20-dione to [17α,16α-d]-2'-methyloxazoline-21-methyl-$\Delta^{1,4,9(11)}$-pregnatriene-3,20-dione, m.p. 202°–205° C.

EXAMPLE 6 a. A solution of 3β,11β-dihydroxy-16β,21-dimethyl-16α,17α-epoxy-5α-pregnan-20-one 11β-acetate from Example 3 (b) (10 g) in dry methanol and methylene chloride was treated with a solution of hydrogen bromide in acetic acid (3.0N; 10 ml) and allowed to stand at room temperature for 24 hours. The solution was diluted with methylene chloride, washed with water, sodium carbonate solution then water to neutrality, dried over sodium sulphate and evaporated to dryness. The residue was crystallised from methylene chloride/methanol to give 3β,11β,17α-trihydroxy-16,21-dimethyl-$\Delta^{15}$-5α-pregnen-20-one 11β-acetate.

Treatment of 3β,11β-dihydroxy-16α,21,21-trimethyl-16α,17α-epoxy-5α-pregnan-20-one 11β-acetate in a similar manner gave 3β,11β,17α-trihydroxy-16,21,21-trimethyl-$\Delta^{15}$-5α-pregnen-20-one 11β-acetate.

b. By the method of Example 1 (h) and (i) 3β11β-trihydroxy-16,21-dimethyl-$\Delta^{15}$-5α-pregnen-20-one 11β-acetate and 3β,11β,17α-trihydroxy-16,21,21-trimethyl-$\Delta^{15}$-5α-pregnen-20-one 11β-acetate were converted via the corresponding 3-ketones to 11β,17α-dihydroxy-16, 21-dimethyl-$\Delta^{1,4,15}$-pregnatriene-3,20-dione 11β-acetate, m.p. 184°–188° C, and 11β,17α-dihydroxy-16,21,21-trimethyl-$\Delta^{1,4,15}$-pregnatriene-3,20-dione 11β-acetate, m.p. 170°–175° C, respectively.

Hydrolysis of the 11β-acetates by the method of Example 3 (e) gave 11β,17α-dihydroxy-16,21-dimethyl-$\Delta^{1,4,15}$-pregnatriene-3,20-dione, m.p. 192°–195° C, and 11β,17α-dihydroxy-16,21,21-trimethyl-$\Delta^{1,4,15}$-pregnatriene-3,20-dione, m.p. 181°–185° C, respectively.

EXAMPLE 7 a. A solution of 3β-hydroxy-$\Delta^{9(11),16}$-5α-pregnadien-20-one acetate (50 g) in methylene chloride (100 ml) was added to an ice-cold solution of excess diazomethane in ether. The solution was allowed to stand in a refrigerator for 4 days, then excess diazomethane was destroyed by the addition of a 10% solution of acetic acid in ether. The solution was evaporated to dryness to give the 16α,17α-pyrazoline.

The crude pyrazoline (56 g) was dissolved in acetone (750 ml) and stirred at room temperature with boron trifluoride etherate (33 ml). After evolution of nitrogen ceased, excess reagent was destroyed with potassium bicarbonate solution and water added to precipitate the product which was filtered, washed with water, and dried. Crystallisation from methylene chloride/methanol gave 3β-hydroxy-16α,17α-methylene-$\Delta^{9(11)}$-5α-pregnen-20-one acetate.

b. The product from Example 7 (a) was hydrolysed with potassium carbonate in warm methanol to give 3β-hydroxy-16α,17α-methylene-$\Delta^{9(11)}$-5α-pregnen-20-one, which was converted by the method of Example 1(h) to 16α,17α-methylene-$\Delta^{9(11)}$-5α-pregnene-3,20-dione.

c. To a stirred suspension of 16α,17α-methylene-$\Delta^{9(11)}$-5α-pregnene-3,20-dione (27.6 g) in methanol (500 ml) was added p-toluenesulphonic acid (0.55 g). After 30 minutes triethylorthoformate (12 ml) was added, followed 5 minutes later by potassium bicarbonate (4 g). The volume of the reaction mixture was reduced to 250 ml and the product precipitated by pouring into water. The dimethyl ketal was filtered and dried. To a stirred solution of lithium diisopropylamide in dry tetrahydrofuran at 0° under nitrogen was added 16α,17α-methylene-$\Delta^{9(11)}$-5α-pregnene-3,20-dione 3,3-dimethyl ketal (31 g) in dry tetrahydrofuran (600 ml). After 30 minutes the reaction mixture was treated with dry methyl iodide (155 ml) and the cooling bath removed. Ten minutes later the mixture was evaporated and the residue dissolved in aqueous acetic acid. This solution was warmed on the steam-bath for 1 hour and the product precipitated with water. Recrystallisation from acetone/ n-hexane gave 16α,17α-methylene-21-methyl-$\Delta^{9(11)}$-5α-pregnene-3,20-dione.

Treatment of 16α,17α-methylene-21-methyl-$\Delta^{9(11)}$-5α-pregnene-3,20-dione, 16α,17α-isopropylidenedioxy-$\Delta^{9(11)}$-5α-pregnene-3,20-dione and 16α,17α-isopropylidenedioxy-21-methyl-$\Delta^{9(11)}$-5α-pregnene-3,20-dione, in a similar manner gave 16α,17α-methylene-21,21-dimethyl-$\Delta^{9(11)}$-5α-pregnene-3,20-dione, 16α,17α-isopropylidenedioxy-21-methyl-$\Delta^{9(11)}$-5α-pregnene-3,20-dione, in a similar manner gave 16α,17α-methylene-21,21-dimethyl-$\Delta^{9(11)}$-5α-pregnene-3,20-dione, 16α,17α-isopropylidenedioxy-21-methyl-$\Delta^{9(11)}$-5α-pregnene-3,20-dione and 16α,17α-isopropylidenedioxy-21,21-dimethyl-$\Delta^{9(11)}$-5α-pregnene-3,20-dione, respectively.

d. By the method of Example 1 (i), (j) and (k) 16α,17α-methylene-21-methyl-$\Delta^{9(11)}$-5α-pregnene-3,20-dione and 16α,17α-methylene-21,21-dimethyl-$\Delta^{9(11)}$-5α-pregnene-3,20-dione were converted to 11β-hydroxy-16α,17α-methylene-21-methyl-$\Delta^{1,4}$-pregnadiene-3,20-dione, m.p. 229°–230° C, and 11β-hydroxy-16α,17α-methylene-21,21-dimethyl-$\Delta^{1,4}$-pregnadiene-3,20-dione, m.p. 221°–225° C, respectively.

EXAMPLE 8 a. To a stirred solution of neutrality 16α,17α-isopropylidenedioxy-21-methyl-$\Delta^{9(11)}$-5α-pregnene-3,20-dione from Example 1 (h) in 20/1 chloroform/acetic acid was added a solution of hydrogen bromide in acetic acid. Bromine (1.1 mole equivalents) as a 10% solution in chloroform was added dropwise. After the addition of sodium acetate solution the organic layer was separated, washed with sodium carbonate solution, then to neutrailty with water, dried and evaporated to give the crude 2α-bromo derivative.

A solution of this product in dimethyl formamide was quickly added to a stirred suspension of lithium bromide and calcium carbonate in dimethyl formamide refluxing in a nitrogen atmosphere.

After 15 minutes the cooled mixture was poured into stirred 1% aqueous acetic acid. After 30 minutes the solid product was filtered off, washed to neutrality with water and dried to give the crude 16α,17α-isopropylidenedioxy-21-methyl-$\Delta^{1,9(11)}$-5α-pregnadiene-3,20-dione.

The product was coverted by the method of Example 1 (i) to 16α,17α-isopropylidenedioxy-21-methyl-$\Delta^{1,4,9(11)}$-pregnatriene-3,20-dione, m.p. 236°–244° C.

In a similar manner 16α,17α-isopropylidenedioxy-21,21-dimethyl-$\Delta^{9(11)}$-5α-pregnene-3,20-dione was converted to 16α,17α-isopropylidenedioxy-21,21-dimethyl-$\Delta^{1,4,9(11)}$-pregnatriene-3,20-dione, m.p. 251°–258° C.

b. To a stirred solution of 16α,17α-isopropylidenedioxy-21-methyl-$\Delta^{9(11)}$-5α-pregnene-3,20-dione from Example 1 (h) in 20/1 chloroform/acetic acid immersed in an ice-bath was added a solution of hydrogen bromide in acetic acid. bromine (2.2 mole equivalents) as a 10% solution in chloroform was then added dropwise. After the addition of sodium bisulphite and sodium acetate solutions the organic layer was separated and washed with sodium carbonate solution, then with water to neutrality, dried and evaporated to give the crude dibromo derivative.

A solution of the crude product in dimethyl acetamide was dehydrobrominated by the method described in Example 8 (a) and the product crystallished from methylene chloride/methanol to give 16α,17α-isopropylidenedioxy-21-methyl-$\Delta^{1,4,9(11)}$-pregnatriene-3,20-dione, m.p. 236°–244° C.

In a similar manner 16α,17α-isopropylidenedioxy-21,21-dimethyl-$\Delta^{9(11)}$-5α-pregnene-3,20-dione was converted to 16α,17α-isopropylidenedioxy-21,21-dimethyl-$\Delta^{1,4,9(11)}$-pregnatriene-3,20-dione, m.p. 251°–258° C.

EXAMPLE 9 a. Ethylene was bubbled through a solution of 3β,11β-dihydroxy-21-methyl-$\Delta^{16}$-5α-pregnen-20-one 3,11-diacetate (10 g) in benzene (250 ml) and the reaction mixture irradiated with ultraviolet light. After 10 hours the reaction was evaporated to dryness and the residue purified by chromatography on silica to furnish 3β,11β-dihydroxy-16α,17α-ethylene-21-methyl-5α-pregnan-20-one 3,11-diacetate.

In a similar manner, 3β,11β-dihydroxy-21,21-dimethyl-$\Delta^{16}$-5α-pregnen-20-one 3,11-diacetate was converted to 3β,11β-dihydroxy-16α,17α-ethylene-21,21-dimethyl-5α-pregnan-20-one 3,11-diacetate.

b. By the method of Example 4 (f) 3β,11β-dihydroxy-16α,17α-ethylene-21-methyl-5α-pregnan-20-one 3,11-diacetate and 3β,11β-dihydroxy-16α,17α-ethylene-21,21-dimethyl-5α-pregnan-20-one 3,11-diacetate gave 3β,11β-dihydroxy-16α,17α-ethylene-21-methyl-5α-pregnan-20-one 11-acetate and 3β,11β-dihydroxy-16α,17α-ethylene-21,21-dimethyl-5α-pregnan-20-one 11-acetate, respectively.

c. By the method of Example 1 (h) 3β,11β-dihydroxy-16α,17α-ethylene-21-methyl-5α-pregnan-20-one 11-acetate and 3β,11β-dihydroxy-16α,17α-ethylene-21,21-dimethyl-5α-pregnan-20-one 11-acetate gave 11β-hydroxy-16α,17α-ethylene-21-methyl-5α-pregnane-3,20-dione 11-acetate and 11β-hydroxy-16α,17α-ethylene-21,21-dimethyl-5α-pregnane-3,20-dione 11-acetate, respectively.

d. By the method of Example 8 (a) 11β-hydroxy-16α,17α-ethylene-21-methyl-5α-pregnane-3,20-dione 11-acetate and 11β-hydroxy-16α,17α-ethylene-21,21-dimethyl-5α-pregnane-3,20-dione 11-acetate gave 11β-hydroxy-16α,17α-ethylene-21-methyl-$\Delta^{1,4}$-pregnadiene-3,20-dione 11-acetate, m.p. 177°–179° C, and 11β-hydroxy-16α,17α-ethylene-21,21-dimethyl-$\Delta^{1,4}$-pregnadiene-3,20-dione 11-acetate, m.p. 200°–201°C, respectively.

Hydrolysis of the 11-acetates by the method of Example 3 (e) gave 11β-hydroxy-16α,17α-ethylene-21-methyl-$\Delta^{1,4}$-pregnadiene-3,20-dione, m.p. 210°–212° C, and 11β-hydroxy-16α,17α-ethylene-21,21-dimethyl-$\Delta^{1,4}$-pregnadiene-3,20-dione, m.p. 188°–190°C, respectively.

EXAMPLE 10 a. 11β-Hydroxy-[17α,16α-d]-2'-methyloxazoline-21methyl-$\Delta^{1,4}$-pregnadiene-3,20-dione (5.2 g) in dimethyl formamide (30 ml) and collidene (10.4 ml) at 10° C was treated dropwise with methanesulphonyl chloride (3.4 ml) and 5% sulphur dioxide in dimethylformamide (5.4 ml). The temperature was allowed to rise to 30° C then cooled to about 10° C and water (5 ml) slowly added. The resulting solution was poured into water (300 ml) containing sodium acetate (8 g), stirred, and the light yellow solid filtered and dried to give [17α, 16α-d]-2'-methyloxazoline-21-methyl-$\Delta^{1,4,9(11)}$-pregnatriene-3,20-dione m.p. 202°–205° C.

Treatment of 11β-hydroxy-[17α,16α-d]-2'-methyloxazoline-21,21-dimethyl-$\Delta^{1,4}$-pregnadiene-3,20-dione, 11β-hydroxy-16α,17α-ethylene-21-methyl-$\Delta^{1,4}$-pregnadiene-3,20-dione and 11β-hydroxy-16α,17α-ethylene-21,21-dimethyl-$\Delta^{1,4}$-pregnadiene-3,20-dione in a similar manner gave [17α, 16α-d]-2'-methyloxazoline-21,21-dimethyl-$\Delta^{1,4,9(11)}$-pregnatriene-3,20-dione, 16α,17α-ethylene-21-methyl-$\Delta^{1,4,9(11)}$-pregnatriene-3,20-dione and 16α,17α-ethylene-21,21-dimethyl-$\Delta^{1,4,9(11)}$-pregnatriene-3,20-dione, respectively.

By the method of Example 1 (j) each of the above four $\Delta^{9(11)}$-compounds was coverted to the corresponding 9α-bromo-11β-hydroxy-compound.

b. A mixture of 9α-bromo-11β-hydroxy-[17α,16α-d]-2'-methyloxazoline-21-methyl-$\Delta^{1,4}$-pregnadiene-3,20-dione (7.39 g), tetrahydrofuran (180 ml), methanol (180 ml) and 1N sodium methoxide/methanol (21.6 ml) was stirred at room temperature. After 15 minutes the excess base was neutralised with acetic acid and poured into water (1.5 liters). The product was filtered and dried to give 9β,11β-epoxy-[17α,16α-d]-2'-methyloxazoline-21-methyl-$\Delta^{1,4}$-pregnadiene-3,20-dione.

Treatment of 9α-bromo-11β-hydroxy-[17α,16α-d]-2'-methyloxazoline-21,21-dimethyl-$\Delta^{1,4}$-pregnadiene-3,20-dione, 9α-bromo-11β-hydroxy-16α,17α-isopropylidenedioxy-21-methyl-$\Delta^{1,4}$-pregnadiene-3,20-dione, 9α-bromo-11β-hydroxy-16α,17α-isopropylidenedioxy-21,21-dimethyl-$\Delta^{1,4}$-pregnadiene-3,20-dione, 9α-bromo-11β-hydroxy-[16α,17α-d]-2'-methyloxazoline-21-methyl-$\Delta^{1,4}$-pregnadiene-3,20-dione, 9α-bromo-11β-hydroxy-16α,17α-methylene-21-methyl-$\Delta^{1,4}$-pregnadiene-3,20-dione, 9α-bromo-11β-hydroxy-16α,17α-methyloxazoline-21,21-dimethyl-$\Delta^{1,4}$-pregnadiene-3,20-dione, 9α-bromo-11β-hydroxy-16α,17α-ethylene-21-methyl-$\Delta^{1,4}$-pregnadiene-3,20-dione and 9α-bromo-11β-hydroxy-16α,17α-ethylene-21,21-dimethyl-$\Delta^{1,4}$-pregnadiene-3,20-dione-and 9αλ bromo-11β-hydroxy 16α,17α in a similar manner gave the corresponding 9β,11β-epoxy-compound, respectively.

c. An ice cold solution of 9β,11β-epoxy-[17α,16α-d]-2'-methyloxazoline (2.6 g) in chloroform (26 ml) was added to a mixture of anhydrous hydrogen fluoride (5.2 g), dry tetrahydrofuran (10.5 ml) and chloroform (5.3 ml) cooled to −30° C. After 2 hours at 0° C the excess hydrogen fluoride was neutralised with potassium carbonate (61 g) in water (600 ml). The product was extracted with ether, washed with water, dried over sodium sulphate and filtered. The filtrate was evaporated to dryness then crystallised from acetone to give 9α-fluoro-11β-hydroxy-[17α,16α-d]-2'-methyloxazoline-21-methyl-$\Delta^{1,4}$-pregnadiene-3,20-dione, m.p. 282°–284° C.

Treatment of 9β,11β-epoxy-[17α,16α-d]-2'-methyloxazoline-21,21-dimethyl-$\Delta^{1,4}$-pregnadiene-3,20-dione, 9β,11β-epoxy-16α,17α-isopropylidene-3,20-dione, 9β,11β-epoxy-16α,17α-isopropylidenedioxy-21-methyl-$\Delta^{1,4}$-pregnadiene-3,20-dione, 9β,11β-epoxy-16α,17α-isopropylidenedioxy-21,21-dimethyl-$\Delta^{1,4}$-pregnadiene-3,20-dione, 9β,11β-epoxy-[16α,17α-d]-2'-methyloxazoline-21-methyl-$\Delta^{1,4}$-pregnadiene-3,20-dione, 9β,11β-epoxy-[16α,17α-d]-2'-methyloxazoline-21,21-dimethyl-$\Delta^{1,4}$-pregnadiene-3,20-dione, 9β,11β-epoxy-16α,17α-methylene-21-methyl-$\Delta^{1,4}$-pregnadiene-3,20-dione, 9β,11β-epoxy-16α,17α-methylene-21,21-dimethyl-$\Delta^{1,4}$-pregnadiene-3,20-dione, 9β,11β-epoxy-16α,17α-ethylene-21-methyl-$\Delta^{1,4}$-pregnadiene-3,20-dione and 9β,11β-epoxy-16α,17α-ethylene-21,21-dimethyl-$\Delta^{1,4}$-pregnadiene-3,20-dione in a similar manner gave 9α-fluoro-11β-hydroxy-[17α,16α-d]-2'-methyloxazoline-21,21-dimethyl-$\Delta^{1,4}$-pregnadiene-3,20-dione, m.p. 264°–265° C, 9α-fluoro-11β-hydroxy-16α17α-isopropylidenedioxy-21-methyl-$\Delta^{1,4}$-pregnadiene-3,20-dione, m.p. 315–327° C (decomp.), 9α-fluoro-11β-hydroxy-16α,17α-isopropylidenedioxy-21,21-dimethyl-$\Delta^{1,4}$-pregnadiene-3,20-dione, m.p. 285°–301° C (decomp.), 9α-fluoro-11β-hydroxy-[16α,17α-d]-2'-methyloxazoline-21-methyl-$\Delta^{1,4}$-pregnadiene-3,20-dione, m.p. 295°–299° C, 9α-fluoro-11β-hydroxy-[16α,17α-d]-2'-methyloxazoline-21,21-dimethyl-$\Delta^{1,4}$-pregnadiene-3,20-dione, m.p. 265°–267° C, 9α-fluoro-11β-hydroxy-16α,17α-methylene-21-methyl-$\Delta^{1,4}$-pregnadiene-3,20-dione, m.p. 223°–225° C, 9α-fluoro-11β-hydroxy-16α,17α-methylene-21, 21-dimethyl-$\Delta^{1,4}$-pregnadiene-3,20-dione, m.p. 251°–258° C, 9α-fluoro-11β-hydroxy-16α17α-ethylene-21-methyl-$\Delta^{1,4}$-pregnadiene-3,20-dione, m.p. 230°–232° C, and 9α-fluoro-11β-hydroxy-16α,17α-ethylene-21,21-dimethyl-$\Delta^{1,4}$-pregnadiene-3,20-dione, m.p. 215°–217° C, respectively.

EXAMPLE 11

A solution of 9α-fluoro-11β-hydroxy-16α,17α-isopropylidenedioxy-21-methyl-$\Delta^{1,4}$-pregnadiene-3,20-dione in acetone was treated with excess 6.24N Jones Reagent. After a few minutes a little isopropanol was added, followed by the slow addition of water. The volatile solvent was removed under vacuum and the solid product was filtered off and crystallised from acetone/hexane to give 9αfluoro-16α, 17α-isopropylidenedioxy-21-methyl-$\Delta^{1,4}$-pregnadiene-3,11,20-trione, m.p. 215°–220° C.

In a similar manner 9α-fluoro-11β-hydroxy-16α,17α-isopropylidenedioxy-21,21-dimethyl-$\Delta^{1,4}$-pregnadiene-3,20-dione was oxidised to 9α-fluoro-16α,17α-isopropylidenedioxy-21,21-dimethyl-$\Delta^{1,4}$-pregnadiene-3,11,20-trione, m.p. 235°–241° C.

Similarly the other 9α-fluoro-11β-hydroxy compounds obtained in Example 10 were oxidised to their corresponding 9α-fluoro-11-ketones. 9α-fluoro-[16α,17α-d]-2'-methyloxazoline-21-methyl-$\Delta^{1,4}$-pregnadiene-3,11,20-trione, $[\alpha]_D^{20} = +189°$ in $CHCl_3$.

EXAMPLE 12

Into a solution of 16α, 17α-isopropylidenedioxy-21-methyl-$\Delta^{1,4,9(11)}$-pregnatriene-3,20-dione (1 g) in 9/1 chloroform/pyridine (50 ml) dry chlorine was passed for 1 minute, and the reaction was then stirred for 30 minutes at room temperature. Excess chlorine was destroyed by the addition of sodium sulphite solution and the mixture was filtered to remove sulphur. The organic phase was washed successively with water, 2N HCl, water, saturated potassium bicarbonate solution and water to neutrality. The dried extract was evaporated to dryness, then the residue was purified on a silica column and crystallised from methanol to give 9α,11β-dichloro-16α,17αisopropylidenedioxy-21-methyl-Δ$^{1,4}$-pregnadien-3,20-dione (630 mg), m.p. 213°–227° C.

In a similar manner 9α,11β-dichloro-16α,17α-methylene-21-methyl-Δ$^{1,4}$-pregnadiene-3,20-dione, 9α,11α-dichloro-[16α,17α-d]-2'-methyloxazoline-21-methyl-Δ$^{1,4}$-pregnadiene-3,20-dione, 9α,11β-dichloro-16α,17α-isopropylidenedioxy-21,21-dimethyl-Δ$^{1,4}$-pregnadiene-3,20-dione, 9α,11β-dichloro-16α,17β-ethylene-21-methyl-Δ$^{1,4}$-pregnadiene-3,20-dione and 9α,11β-dichloro-16,16-methylene-17α-hydroxy-21-methyl-Δ$^{1,4}$-pregnadiene-3,20-dione were prepared from the corresponding Δ$^{9(11)}$-compounds.

EXAMPLE 13

16α,17α-methylene-21-methyl-Δ$^{1,4,9(11)}$-pregnatriene-3,20-dione (800 mg) were dissolved in 10% aqueous dioxan (35 ml), cooled to 10° C and 72% perchloric acid (0.2 ml) was added followed by N-chloro succinimide (0.5 g) and the reaction stirred overnight. The product was watered out, filtered, dried and recrystallised from methylene chloride to give 9α-chloro-11β-hydroxy-16α,17α-methylene-21-methyl-Δ$^{1,4}$-pregnadiene-3,20-dione (550 mg).

EXAMPLE 14

A solution of [16α,17α-d]-2'-methyloxazoline-21-methyl-Δ$^{1,4,9(11)}$-pregnatriene-3,20-dione (1 g) in chloroform (30 ml) and pyridine (5 ml) was treated with a solution of HF (1.5 g) in tetrahydrofuran (5ml) and chloroform (2 ml) followed by N-chlorosuccinimide (0.5 g). After a week at room temperature the reaction was poured into excess 10% sodium acetate solution and the product isolated via methylene chloride. The crude product was purified on a silica gel and crystallised from ether to give 9α-chloro-11β-fluoro-[16α,17α-d]-2'-methyloxazoline-21-methyl-Δ$^{1,4}$-pregnadiene-3,20-dione (0.5 g).

EXAMPLE 15

11β-Hydroxy-16α,17α-isopropylidenedioxy-21-methyl-Δ$^{1,4}$-pregnadiene-3,20-dione 11-acetate (2 g) and dichlorodicyanoquinone (1.3 g) were dissolved in dioxan (35 ml). Hydrogen chloride was passed into the solution until a precipitate started to form and the reaction mixture was allowed to stand for a further 20 minutes. The solid was removed by filtration and the filtrate was poured into aqueous sodium carbonate solution. The product was isolated via ether and purified by chromatography on silica gel to give 11β-hydroxy-16α,17α-isopropylidenedioxy-21-methyl-Δ$^{1,4,6}$-pregnatriene-3,20-dione 11-acetate (1.2 g) as an amorphous solid.

EXAMPLE 16

By the method of Examples 1 (d)-g) 3β-hydroxy-21-methyl-Δ$^{5,16}$-pregnadien-20-one was converted to 3β-hydroxy-16α,17α-isopropylidenedioxy-21-methyl-Δ$^{5}$-pregnen-20-one. A solution of this Δ$^{5}$-compound (5 g) in chloroform (50 ml) was stirred with peracetic acid (5 ml) and sodium acetate (0.5 g) for one hour, after which excess peracid was destroyed with sodium bisulphite. Further processing gave 3β-acetoxy-5α-6α-epoxy-16α,17α-isopropylidenedioxy-21-methyl-5α-pregnan-20-one. Treatment of this compound with borontrifluoride etherate/HF gave 3β-acetoxy-5α-hydroxy-6β-fluoro-16α,17α-isopropylidenedioxy-21-methyl-5α-pregnan-20-one, which after hydrolysis of the 3β-acetoxy group and oxidation of the 3β-hydroxy group with Jones' reagent to the 3-keto group, was dehydrated and isomerised in acetic acid/HCl to 6α-fluoro-16α,17α-isopropylidenedioxy-21-methyl-Δ$^{4}$-pregnene-3,20-dione. The latter compound was refluxed in benzene with DDQ for 15 hours to give 6α-fluoro-16α,17α-isopropylidenedioxy-21-methyl-Δ$^{1,4}$-pregnadiene-3,20-dione, m.p. 283°–290° C.

We claim:

1. 11β-Hydroxy-16α, 17α-isopropylidenedioxy-21-methyl-Δ$^{1,4}$-pregnadiene-3,20-dione.

2. An alkylated 3,20-diketo-Δ$^{4}$-steroid of the pregnane series having the formula:

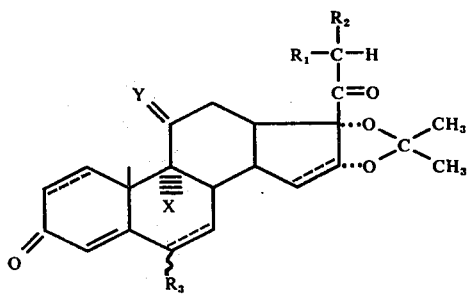

wherein X is a member of the group consisting of H, F and Cl; Y is a member of the group consisting of H$_2$, H(OH), O and H(Cl); R$_1$ is methyl; R$_2$ is a member of the group consisting of H and methyl; R$_3$ is a member of the group consisting of H, F and methyl.

3. 9α-Fluoro-11β-hydroxy-16α,17α-isopropylidenedioxy-21-methyl-Δ$^{1,4}$-pregnadiene-3,20-dione.

4. 9α-Fluoro-16α,17α-isopropylidenedioxy-21-methyl-Δ$^{1,4}$-pregnadiene-3,11,20-trione.

5. 9α,11β-Dichloro-16α,17α-isopropylidenedioxy-21-methyl-Δ$^{1,4}$-pregnadiene-3,20-dione.

6. 6α-Fluoro-16α,17α-isopropylidenedioxy-21-methyl-Δ$^{1,4}$-pregnadiene-3,20-dione.

* * * * *

UNITED STATES PATENT AND TRADEMARK OFFICE
CERTIFICATE OF CORRECTION

PATENT NO. : 4,031,075
DATED : June 21, 1977
INVENTOR(S) : Gilbert F. Woods et al.

It is certified that error appears in the above-identified patent and that said Letters Patent are hereby corrected as shown below:

Column 1, line 6, the phrase "and now abandoned" should not be in bold face type.

Column 3, line 65, "-alkylideen" should read -- -alkylidene --.

Column 4, line 44, "16α,17β" should read -- 16β,17β --.

Column 6, line 16, "$66^4$" should read -- $\Delta^4$ --.

Column 13, line 45, "-one," should read -- -one --.

Column 14, line 26, "$66^{16}$" should read -- $\Delta^{16}$ --; line 42, "into" should read -- onto --; line 45, "-one," should read -- -one --; line 49, there should be only a single space between " -20-one" and "3,11,16-"; and line 65, "-one," should read -- -one --.

Column 15, line 36, "C.1" should read -- C. --.

Signed and Sealed this

Third Day of January 1978

[SEAL]

Attest:

RUTH C. MASON
*Attesting Officer*

LUTRELLE F. PARKER
*Acting Commissioner of Patents and Trademarks*